(12) United States Patent
Fotinos et al.

(10) Patent No.: US 10,377,114 B2
(45) Date of Patent: *Aug. 13, 2019

(54) METHOD FOR MAKING A TRANSDERMAL FENTANYL PATCH WITH EVEN DRUG CRYSTAL DISTRIBUTION

(71) Applicant: INEP EUROPE SARL, Luxembourg (LU)

(72) Inventors: Spiros Fotinos, Attika (GR); Jerome Langlume, Paris (FR); Jean Paul Caravita, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/492,146

(22) Filed: Apr. 20, 2017

(65) Prior Publication Data

US 2018/0303766 A1    Oct. 25, 2018

(51) Int. Cl.

| | | |
|---|---|---|
| *A61K 31/4468* | (2006.01) | |
| *A61K 9/70* | (2006.01) | |
| *C08L 83/04* | (2006.01) | |
| *C09J 183/04* | (2006.01) | |
| *B32B 27/36* | (2006.01) | |
| *A61K 31/00* | (2006.01) | |
| *B32B 7/06* | (2019.01) | |
| *B32B 27/22* | (2006.01) | |
| *B32B 27/24* | (2006.01) | |

(52) U.S. Cl.
CPC ............ *B32B 27/36* (2013.01); *A61K 9/7069* (2013.01); *A61K 9/7084* (2013.01); *A61K 31/00* (2013.01); *A61K 31/4468* (2013.01); *B32B 7/06* (2013.01); *B32B 27/22* (2013.01); *B32B 27/24* (2013.01)

(58) Field of Classification Search
None
See application file for complete search history.

(56) References Cited

U.S. PATENT DOCUMENTS

| | | |
|---|---|---|
| 4,588,580 A | 5/1986 | Gale et al. |
| 7,247,315 B2 | 7/2007 | Brown et al. |
| 2012/0209223 A1* | 8/2012 | Salman ................ A61K 9/7023 604/307 |

* cited by examiner

*Primary Examiner* — Abigail Vanhorn
(74) *Attorney, Agent, or Firm* — Porzio Bromberg & Newman P.C.

(57) ABSTRACT

Methods of producing a transdermal delivery patches are described comprising the preparation of a uniform suspension of drug particles. A plasticizer is added to the suspension. A solution of an adhesive is add to the suspension to form a drug suspension in the adhesive mixture. The drug suspension is coated on a release liner and all solvents are evaporated to form a solid drug reservoir layer. A medical device for transdermal administration of a drug can include the solid drug reservoir layer. Suitable drugs include fentanyl and sufentanil.

8 Claims, 1 Drawing Sheet

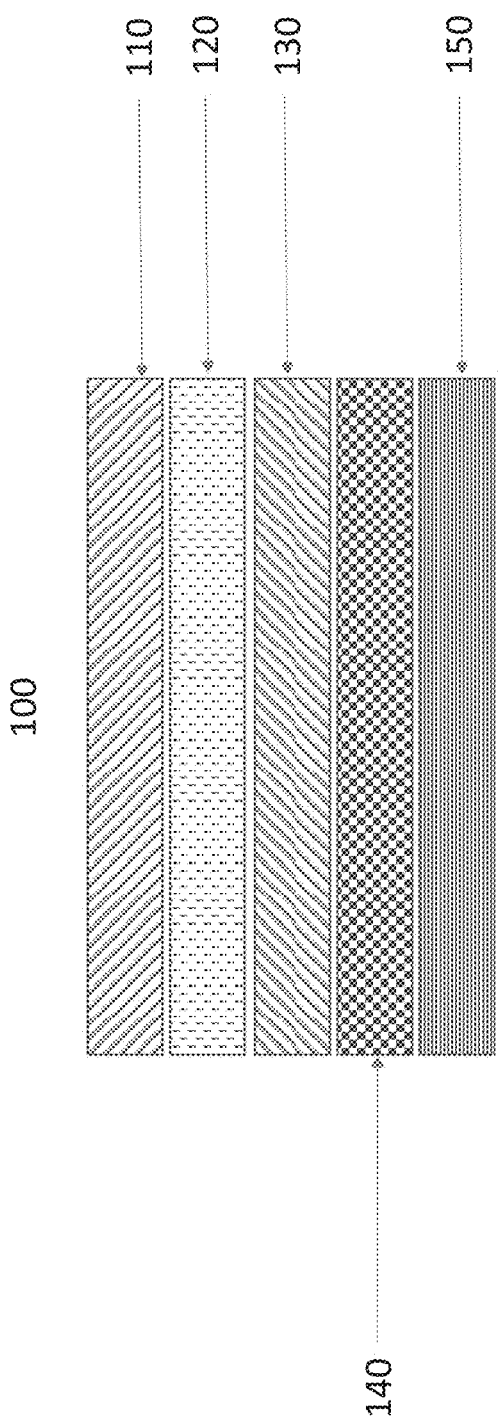

METHOD FOR MAKING A TRANSDERMAL FENTANYL PATCH WITH EVEN DRUG CRYSTAL DISTRIBUTION

BACKGROUND OF THE INVENTION

Field of the Invention

The present invention relates to a transdermal fentanyl patch with even drug crystal distribution.

Description of Related Art

A conventional transdermal delivery patch has been described in U.S. Pat. No. 7,247,315. The patch includes a solid drug reservoir medical device for transdermal administration of a drug. The medical device has four layers, from top to bottom, a backing, a solid drug reservoir, a rate-controlling membrane, and an adhesive layer. The adhesive layer is covered with a release liner. The physical structure of this device is similar to a liquid reservoir fentanyl patch as described in U.S. Pat. No. 4,588,580. The main difference in structure between the solid reservoir patch and the fentanyl patch described in U.S. Pat. No. 4,588,580 is that the reservoir layer of the original fentanyl patch was primarily liquid in composition, while the reservoir of U.S. Pat. No. 7,247,315 is a solid adhesive material. The liquid reservoir of the fentanyl patch described in U.S. Pat. No. 4,588,580 is contained physically within the patch by a peripheral seal around the edge of the patch, joining the backing to the rate-controlling membrane at the edges, sealing the liquid reservoir between the backing and the rate-controlling membrane. No peripheral seal is needed for the solid reservoir patch described in U.S. Pat. No. 7,247,315.

The process for manufacturing the device of U.S. Pat. No. 7,247,315 includes a step for manufacturing the solid drug reservoir by which the active ingredient, fentanyl base, was present in solution with the adhesive in the coating composition that was used to produce the solid adhesive reservoir. The drug/adhesive solution was applied to a substrate and passed through an oven to evaporate the solvent. After this coated drug adhesive composition exited the coating oven, with low levels of residual solvent after evaporation, the drug recrystallized within the solid drug reservoir. The resulting composition contained recrystallized drug in a form that was not well-defined when viewed microscopically. The drug particles were small and formed agglomerates. Although the amount of drug in any specified area was controlled at the scale of the smallest dosage of the product, the size and distribution of the drug particles within the patch appeared non-uniform when viewed microscopically, due to the formation of agglomerates. The agglomeration of the drug particles makes it difficult to characterize accurately the size of the drug particles within the patch. The fentanyl patch described in U.S. Pat. No. 4,588,580 has high variation in the size of the individual drug particles and high variation in the physical distribution of the drug particles within the liquid reservoir as demonstrated by the photomicrograph.

Development Principles for passive transdermal systems have been published in AAPS PharmSciTech (DOI: 10.1208/s12249-011-9740-9) which cite a requirement to test particle size of drug for evidence of particle size alteration. Criteria for the testing include appearance of particles and changes in particle form, size, shape, habit, or aggregation that may occur during the course of product processing and storage. This testing is difficult to perform when the product is manufactured by the process described in U.S. Pat. No. 7,247,315. A method is described for producing the solid drug reservoir layer in U.S. Pat. No. 7,247,315, hereby incorporated by reference into this application. The drug is dispersed in isopropanol (IPA). A dimethicone, such as Medical Fluid, is added and mixed. Silicone adhesive in heptane is then added, and the mixture is stirred until clear, thereby assuring the drug is dissolved in this mixture.

It is desirable to provide a fentanyl patch having a composition including a drug-containing layer of the patch manufactured in a manner so that the appearance of drug particles in the product is controlled and the drug particles can be characterized according the Development Principles for passive transdermal systems.

SUMMARY OF THE INVENTION

The present invention provides a method of manufacture for a composition suitable for use in a medical device that does not include a process step by which complete dissolution of the drug occurs.

The method of manufacture for a composition suitable for use in a medical device of the present invention includes the step of producing a solid drug reservoir layer for use in the medical device. By the method of the present invention, the drug is first dispersed in a solvent in a ratio of about 2:1 or 3:1 For example, the drug can be dispersed in heptane, at a ratio of about 2:1 or 3:1 heptane:drug w/w. This mixture is stirred to blend the drug uniformly in the dispersion with heptane. A suitable drug is fentanyl. Fentanyl has a finite solubility in heptane. This suspension is added quantitatively to an adhesive solution. In one embodiment, after mixing of the dispersion for a suitable time, a dimethicone, such as Medical Fluid, can be added to the dispersion, and the dispersion. An analysis of heptane from a sample of this mixture after the undissolved drug is separated by filtration provides a measure of the amount of the fentanyl that has dissolved in the heptane. In the adhesive mixture of the present invention, there is no IPA present in the mixture. The drug is suspended in the adhesive mixture rather than dissolved. The drug adhesive solution mixture is then coated on a backing layer, forming a drug reservoir layer after evaporation of the solvent. By this process, crystalline drug is present within the drug reservoir layer immediately after the coating process.

The medical device produced by the method of the present invention is for transdermal administration of a drug through an area of human skin during an administration period.

In the present invention, the drug may be micronized prior to suspension in the heptane. In this manner, the particle size of the drug in the product may be controlled through control of particle size of the raw material active pharmaceutical ingredient (API) input to the process in the suspension with heptane. The drug particles in the finished product are not larger than the initial particle size of the drug as it is suspended in the heptane.

By the process of the present invention the drug does not re-crystallize in the drug adhesive after coating. The crystalline drug particles in the drug adhesive remain in the same form and remain crystalline throughout the entire process.

BRIEF DESCRIPTION OF THE DRAWINGS

The FIGURE is a schematic illustration of a solid reservoir transdermal drug delivery device of the present invention.

DETAILED DESCRIPTION

The present invention relates to a drug containing composition that can be manufactured in a manner that provides control of the particle size of the drug in the finished product through control of the particle size of the active pharmaceutical ingredient (API) input to the process. The process of the present invention results in a very even distribution of the drug particles in a solid drug adhesive layer as viewed and measured by microscopy. This improved process allows characterization of the appearance of drug particles, changes in particle form, size, shape, habit, or aggregation that may occur during the course of product processing and storage, as specified in Development Principles in AAPS PharmSciTech (DOI: 10.1208/s12249-011-9740-9).

A preferred method for preparing the drug-containing compositions of the present invention comprises micronizing a raw material active pharmaceutical ingredient (API) to a specified particle size/distribution. The raw material active pharmaceutical ingredient (API) can be fentanyl and analgesically effective derivatives thereof as the drug, it should be understood that other drugs are also suitable for use with the teachings of the present invention including: sufentanil oxymorphone, oxycodone, hydromorphone, morphine, buprenorphine and analgesically effective derivatives thereof.

The particle size is selected based on several criteria. First, the particle size/distribution should be small so that the finished product contains particles with high specific surface area so that dissolution from drug particles does not limit the rate of drug release from the finished product. Second, the drug particles should be small enough so that all particles pass easily through all apertures present in the manufacturing process, such as the gap in the coating die. Third, the drug particles should be small enough so that any tendency for settling of drug particles in suspension is minimized. Finally, the drug particles should not be so small that there is difficulty in transfer of the raw material to the suspension (no aerosolization). The particle size distribution should be chosen so that no particles are greater in size than about 40 microns and the D(90) particle size distribution is greater than about 3 microns.

An adhesive is received in a solution with a solvent to form an adhesive solution. For example, the solvent can be heptane. Alternatively, the adhesive and solvent can be received separately, and dissolution of the adhesive in the solvent will be an additional step in the process. Example adhesives include amine resistant silicone adhesive. Examples of suitable amine resistant silicone adhesive matrix material compositions include any type of "high tack" polydimethylsiloxane with an average molecular weight of between 100,000 and 5,000,000, preferably 500,000 and 1,500,000.

The micronized fentanyl or sufentanil is added to a quantity of solvent, for example heptane. The micronized fentanyl or sufentanil is first dispersed in a solvent in a ratio of about 2:1 or 3:1. For example, the micronized fentanyl or sufentanil can be dispersed in heptane, at a ratio of about 2:1 or 3:1 heptane:fentanyl or heptane:sufentanil w/w. This mixture is stirred to blend the fentanyl or sufentanil uniformly in the dispersion with heptane to create uniform suspension of the fentanyl or sufentanil in the solvent. The dispersion of fentanyl or sufentanil in dispersion is quantitatively added to the adhesive solution to transfer substantially all of the fentanyl and sufentanil in dispersion to the adhesive solution.

A quantity of plasticizer can be added to the suspension, at the proper ratio, so that when the solvent is removed by evaporation the plasticizer will be present in the dried adhesive at the correct concentration. Particularly preferred plasticizers include low molecular weight polydimethylsiloxane described in the National Formulary as Dimethicone with a viscosity of between 20 and 12,500 centistoke, and preferably between 300 and 400 centistoke. The solvent should be selected so that the fentanyl or sufentanil particles become suspended in the solvent; and, when the suspension of fentanyl in the solvent with plasticizer is added to the adhesive solution, the drug particles remain suspended without dissolving and the adhesive remains dissolved.

The dispersion of fentanyl or sufentanil in solvent and plasticizer is then mixed with the adhesive solution. Suspended drug particles are visible in this mixture. Because the drug is dispersed rather than dissolved in this mixture, it is necessary to assure the drug is uniformly distributed in the mixture during the subsequent processing step (coating) in which the mixture is metered through a casting die, deposited on a moving web, and passed through an oven to evaporate the solvent. Mixing of this mixture can continue during this coating step.

The medical device produced by the method of the present invention is for transdermal administration of a drug through an area of human skin during an administration period. The medical device comprising:

a solid drug reservoir layer having a top side and a bottom side and an external edge, wherein the solid drug reservoir layer is a composition formed by the method of the present invention;

a rate-controlling membrane having a top and a bottom side, wherein the top side of the rate-controlling membrane is contiguously disposed with respect to the bottom side of the solid drug reservoir layer; and an adhesive layer having a top and a bottom side, wherein the top side of the adhesive layer is contiguously disposed with respect to the bottom side of the rate-controlling membrane.

In some embodiments, the present invention provides a multilaminate medical device. Referring to The FIGURE, a schematic illustration of a multilaminate transdermal drug delivery device 100 embodiment of the present invention comprises a backing layer 110, a drug reservoir layer 120, a rate controlling membrane 130, an adhesive layer 140 and a strippable release liner 150. The backing layer 110 can be any backing layer described above, such as a 1-5 mil thick multilaminate comprising PET and EVA. In some embodiments, the backing layer 110 can be impermeable to liquids from outside medical device. The solid drug reservoir layer 120 comprises a matrix material such as an amine resistant silicone adhesive and a fentanyl flux rate lowering amount of one or more suitable plasticizer(s) such as polydimethylsiloxane (e.g., Medical Fluid 360 from Dow Corning). The solid drug reservoir composition also has a dissolved and suspended drug within the solid drug reservoir layer 120. Preferably, the drug composition is fentanyl, a fentanyl derivative, or a pharmaceutically acceptable salt thereof. The peripheral edge 122 of the solid drug reservoir layer 120 is unsealed, and can be exposed to air, in the medical device product of the invention shown in The FIGURE. The rate controlling membrane 130 comprises low density polyethylene, polyethylene-(vinyl acetate) copolymers (with up to 40% vinyl acetate, preferably between 5 and 19% vinyl acetate, and most preferably 19% vinyl acetate). The thickness of the rate controlling membrane 130 can be adjusted with the 20 percent vinyl acetate in the composition to provide a selected fentanyl flux rate, as discussed above. The rate controlling membrane 130 is between about 0.5 to 5.0 mils (that is, about 0.0127 to 0.1270 inches) thick. The adhesive layer 140 is comprised of the same matrix material composition and a similar type of flux rate lowering plasticizer as the solid drug reservoir composition 120. The adhesive layer 140 comprises a flux rate lowering effective amount of the plasticizer(s) present in the solid drug reservoir layer 120. Most preferably, the adhesive layer 140 comprises the same plasticizer(s) present in the solid drug reservoir layer 120 in approximately the same weight percentage(s). The strippable release liner 150 can be any release liner described above, such as a 3 mil thick fluorocarbon diacrylate or silicone (polysiloxane) coated polyester film. The various layers are laminated or otherwise assembled into a transdermal drug delivery device, such as a bandage or patch, having a medically appropriate predetermined size and shape as known in the art. While The FIGURE describes a preferred embodiment, it should be recognized that one or more of the layers may be deleted or repeated, the basic transdermal system being a drug containing matrix material comprising the fentanyl flux rate lowering composition of the invention provided and maintained in drug transferring effective relationship with the skin. In particularly preferred embodiments comprising both an adhesive layer 140 and a solid drug reservoir layer 120, both layers preferably comprise matrix materials and plasticizer(s) that are similar in type and amount.

A monolith medical device for trans dermal drug delivery comprises a backing layer, a drug reservoir adhesive layer and a strippable release liner. The backing layer can be any backing layer described above, such as a 1-5 mils thick multi laminate comprising PET and EVA. In some embodiments, the backing layer can be impermeable to liquids from outside medical device. The drug reservoir adhesive layer comprises a matrix material such as an amine resistant silicone adhesive and a fentanyl flux rate lowering amount of one or more suitable plasticizer(s) such as a polydimethylsiloxane emulsion (e.g., Medical Fluid 360 from Dow Corning). For example, the drug reservoir adhesive layer can comprise about 70-95% w/w of a polysiloxane-based adhesive matrix material, about 4-20% w/w polydimethylsiloxane-type plasticizer and about 2-15% w/w of the fentanyl drug composition. The drug reservoir adhesive layer in a monolith medical device can serve as both a solid drug reservoir and as an adhesive layer to maintain the monolith medical device in transdermal drug flux permitting contact with a subject's skin throughout an administration period. The drug reservoir adhesive layer composition has a dissolved and suspended drug within the drug reservoir adhesive layer. Preferably, the drug composition is fentanyl, a fentanyl derivative, or a pharmaceutically acceptable salt thereof. The peripheral edge of the drug reservoir adhesive layer is unsealed, and can be exposed to air.

The product manufactured by the present invention has the following attributes:

1) the appearance of drug particles in the product is controlled, and the drug particles can be characterized according the Development Principles described in AAPS PharmSciTech (DOI: 10.1208/s12249-011-9740-9), hereby incorporated by reference in its entirety into this disclosure.

2) the drug particles in the product are small and evenly distributed in the product in comparison to other fentanyl patches.

3) the drug particles are present in the solid drug reservoir layer of the patch and not in the second adhesive layer, the skin adhesive, below the rate-controlling membrane 4) the crystalline form of the drug particles in the product is the same as the crystalline form of the raw material API input to the process.

It is to be understood that the above-described embodiments are illustrative of only a few of the many possible specific embodiments, which can represent applications of the principles of the invention. Numerous and varied other arrangements can be readily devised in accordance with these principles by those skilled in the art without departing from the spirit and scope of the invention.

What is claimed is:

1. A medical device for transdermal administration of a drug comprising:
   a solid drug reservoir layer formed by the steps of:
   micronizing fentanyl to a particle size of less than about 40 microns;
   dispersing the micronized fentanyl in a first solvent to form a uniform suspension of particles of fentanyl, the first solvent is heptane;
   adding a first plasticizer to the uniform suspension of particles of fentanyl;
   forming an adhesive solution of an adhesive and a second solvent, the second solvent is heptane; and where the adhesive consists of a silicone adhesive; and
   adding the uniform suspension of particles of fentanyl quantitatively to the adhesive solution to add the particles of fentanyl from the uniform suspension to the adhesive solution, all the particles of fentanyl suspended in the uniform suspension are crystalline particles having a particle size which is not larger than an initial particle size of the fentanyl, wherein when the suspension of particles of fentanyl in the heptane with plasticizer is added to the adhesive solution, the fentanyl particles remain suspended without dissolving.

2. The medical device of claim 1 wherein the D(90) particle distribution is greater than about three microns.

3. The medical device of claim 1 wherein the fentanyl is added in a ratio of about 2:1 or 3:1 of the heptane to the fentanyl w/w.

4. The medical device of claim 1 wherein the first plasticizer is polydimethylsiloxane matrix material.

5. The medical device of claim 1 wherein the suspension of particles of fentanyl in the adhesive mixture is coated on a release liner and the first and second solvent are evaporated to form the solid drug reservoir on the release liner.

6. The medical device of claim 1 further comprising:
   a rate-controlling membrane having a top and a bottom side, wherein the top side of the rate-controlling membrane is contiguously disposed with respect to the bottom side of the solid drug reservoir layer; and
   an adhesive layer having a top and a bottom side, wherein the top side of the adhesive layer is contiguously disposed with respect to the bottom side of the rate-controlling membrane.

7. The medical device of claim 1 wherein the fentanyl comprises 2-15% w/w of a composition of the solid drug reservoir layer.

8. The medical device of claim 1 wherein the first plasticizer is a polydimethylsiloxane-type plasticizer and comprises 4-20% w/w of a composition of the solid drug reservoir layer.

* * * * *